(12) United States Patent
Kang et al.

(10) Patent No.: US 7,435,414 B2
(45) Date of Patent: Oct. 14, 2008

(54) HUMANIZED ANTIBODY AGAINST S-SURFACE ANTIGEN OF HEPATITIS B VIRUS

(75) Inventors: Heui Il Kang, Seoul (KR); Byung Kyu Lee, Gunpo-si (KR); Se Cheol Park, Seoul (KR); Moo Young Song, Suwon-si (KR); Tae Hyoung Yoo, Seoul (KR); Jae Sun Lee, Suwon-si (KR); Chang Seok Kim, Suwon-si (KR); Sang Koo Park, Suwon-si (KR); Kang In Na, Suwon-si (KR)

(73) Assignee: Yuhan Corporation, Seoul (KR)

( * ) Notice: Subject to any disclaimer, the term of this patent is extended or adjusted under 35 U.S.C. 154(b) by 371 days.

(21) Appl. No.: 11/100,553

(22) Filed: Apr. 7, 2005

(65) Prior Publication Data

US 2006/0014937 A1 Jan. 19, 2006

(30) Foreign Application Priority Data

Apr. 14, 2004 (KR) ...................... 10-2004-0025573

(51) Int. Cl.
*A61K 39/395* (2006.01)
(52) U.S. Cl. .................................................. 424/133.1
(58) Field of Classification Search ........................ None
See application file for complete search history.

(56) References Cited

U.S. PATENT DOCUMENTS

| | | | | |
|---|---|---|---|---|
| 6,680,053 B2* | 1/2004 | Lee et al. | .................. | 424/149.1 |
| 6,924,368 B2* | 8/2005 | Lee et al. | .................. | 536/23.53 |
| 7,112,664 B2* | 9/2006 | Lee et al. | .................... | 536/23.1 |

FOREIGN PATENT DOCUMENTS

WO    WO 01/92529    * 12/2001

OTHER PUBLICATIONS

J. Summers et al., "Genome of hepatitis B virus: Restriction enzyme cleavage and structure of DNA extracted from Dane particles", *Proc. Nat. Acad. Sci.*,, vol. 72, No. 11, Nov. 1975, pp. 4597-4601.
P. Tiollais et al., "Biology of Hepatitis B virus", *Science*, vol. 213, Jul. 24, 1981, pp. 406-411.
C.L. Lai et al., "Antiviral treatment for chronic hepatitis B", *HKMJ*, vol. 3, No. 3, Sep. 1997, pp. 289-296.
D. T.-Y. Lau et al., "Long-Term Therapy of Chronic Hepatitis B With Lamivudine", *Hepatology*, Oct. 2000, pp. 828-834.
J.J. Dimaggio et al., "Monoclonal antibody therapy of cancer", *Cancer Chemotherapy and Biological Response Modifiers Annual 11*, Chapter 12, 1990, pp. 177-203.
L. Riechmann et al., "Reshaping human antibodies for therapy", *Nature*, vol. 332, Mar. 24, 1988, pp. 323-327.
T. Nakatani et al., "Humanization of mouse anti-human IL-2 receptor antibody B-B10", *Protein Engineering*, vol. 7, No. 3, 1994, pp. 435-443.
P. Carter et al., "Humanization of an anti-p185$^{HER2}$ antibody for human cancer therapy", *Proc. Natl. Acad. Sci.*, vol. 89, May 1992, pp. 4285-4289.
K. Kawasaki et al., "One-Megabase Sequence Analysis of the Human Immunoglobulin λ Gene Locus", *Genome Research*, vol. 7, 1997, pp. 250-261.
E.A. Kabat et al., "Sequences of Proteins of Immunological Interest," 5$^{th}$ edition, D.H.H.S. NIH Publication No. 91-3242, 1991.
C. Chothia et al., "Conformations of immunoglobulin hypervariable regions", *Nature*, vol. 342, Dec. 21/28, 1989, pp. 877-883.
G. Studnicka et al., "Human-engineered monoclonal antibodies retain flull specific binding activity by preserving non-CDR complementarity-modulating residues", *Protein Engineering*, vol. 7, No. 6, 1994, pp. 805-814.
L. Harris et al., "Profiles for the analysis of immunoglobulin sequences: Comparison of V gene subgroups", *Protein Science*, vol. 4, 1995, pp. 306-310.
M. Kozak, "An analysis of 5'-noncoding sequences from 699 vertebrate messenger RNAs", *Nucleic Acids Research*, vol. 15, No. 20, 1987, pp. 8125-8148.
B. Friguet et al., "Measurements of the True Affinity Constant in Solution of Antigen-Antibody Complexes by Enzyme-Linked Immunosorbent Assay", *Journal of Immunological Methods*, vol. 77, 1985, pp. 305-319.
Korean Patent Abstracts of Korean Patent Laid-Open Publication No. 10-2004-12266 published Feb. 11, 2004.
Korean Patent Abstracts of Korean Patent Laid-Open Publication No. 10-2004-12267 published Feb. 11, 2004.

* cited by examiner

*Primary Examiner*—Bruce Campell
*Assistant Examiner*—Nicole Kinsey White
(74) *Attorney, Agent, or Firm*—Sughrue Mion, PLLC

(57) ABSTRACT

A humanized antibody of the present invention shows similar antigen-binding affinity to a mouse monoclonal antibody and significantly low immunogenecity. Therefore, the humanized antibody of the present invention can be effectively used for treating chronic hepatitis B and preventing HBV infection of a patient received liver transplantation and vertical transmission from a mother infected with HBV to a fetus.

11 Claims, 4 Drawing Sheets

FIG. 1

```
              1         10        20        30         40        50   x
A9-11-5:QVQLKQSGPGLVQPSQSLSITCTVSGFSLS TYGVQ WVRQSPGKGLEWLG VIWSGGNT
   Hh2 :QVQLQESGPGLVKPSQTLSLTCTVSGGSVS S-YWS WIRQPPGKGLEWIG -IY-SG-T
HFW141:QVQLKQSGPGLVKPSQTLSLTCTVSGFSLS TYGVQ WVRQPPGKGLEWLG VIWSGGNT 60        70         80   abc       90    x100a      110  113
A9-11-5:DYNAAFIS RLSISKDNSKNQVFFKVNSLQADDTAIYYCAR ARYFDV WGAGTTVTVSS
   Hh2 :-YNPSLKS RVTISVDTSKNQFSLKLSSVTAADTAVYYCAR
HFW141:DYNAAFIS RVTISKDTSKNQVSLKLSSVTAADTAVYYCAR ARYFDV WGAGTTVTVSS
```

FIG. 2

```
              1         10        20    24   X  30X       40        50
 A9-11-5:QAVVTQESALTTSPGETVTLTC RSSTGAITTNNFAN WVQEKPDHLFTGLIG DTNNRVP
    hV7:QAVVTQEPSLTVSPGGTVTLTC GSSTGAVTSDHYPY WFQQKPGQAPRTLIY DTSNKHS
LFW22-31:QAVVTQEPSLTVSPGGTVTLTC RSSTGAITTNNFAN WFQQKPGQAFRGLIG DTNNRVP
LFW22-312:QAVVTQEPSLTVSPGGTVTLTC RSSTGAITTNNFAN WFQQKPGQAFRGLIG DTNNRVP
                                          -

60        70        80        90       100      107
 A9-11-5:GVPARFSGSLIGDKAALTITGAQTEDEAIYFC ALW YN NNV FGGGTKLTVLG
    hV7:WTPARFSGSLLGGKAALTLLGAQPEDEAEYYC LLS YS G     AR
LFW22-31:GVPARFSGSLLGNKAALTITGAQPEDEAEYYC ALW YN NNV FGGGTKLTVLG
LFW22-312:GVPARFSGSLIGDKAALTITGAQPEDEAEYYC ALW YN NNV FGGGTKLTVLG
```

HUMANIZED ANTIBODY AGAINST S-SURFACE ANTIGEN OF HEPATITIS B VIRUS

This is a Non-provisional application which claims priority under 35 U.S.C. § U.S.C. § 119 from Korean Patent Application No. 10-2004-0025573 filed Apr. 14, 2004.

FIELD OF THE INVENTION

The present invention relates to a humanized antibody against S-surface antigen of hepatitis B virus (hereinafter, referred to as "HBV"), a method for the preparation thereof, and a pharmaceutical composition for treating HBV-relating diseases comprising the humanized antibody.

BACKGROUND OF THE INVENTION

HBV well-known as a Dane particle is a spherical particle having a diameter of about 42 nm and composed of an outer envelope and a nucleocapsid. The outer envelope surrounding the nucleocapsid contains a large quantity of hepatitis B surface antigens, and the nucleocapsid comprising about 180 subunits of hepatitis B core protein includes several kinds of genes encoding HBV structural proteins, polymerase and so on (Summers et al., Proc. Nat. Acad. Sci. 72: 4579, 1975; Pierre Tiollais et al., Science 213: 406-411, 1981).

The gene coding region of HBV surface antigens contains three in-frame initiation sites, and all these sites share a termination codon of S-domain terminal. Therefore, the HBV surface antigens can be divided into three groups: (i) a small hepatitis B virus surface antigen (hereinafter, referred to as "S-surface antigen") containing only the S-domain; (ii) a middle hepatitis B virus surface antigen (hereinafter, referred to as "M-surface antigen") containing the S-domain and Pre-S2 consisting of 55 amino acids; and (iii) a large hepatitis B virus surface antigen (hereinafter, referred to as "L-surface antigen") containing the S-domain, Pre-S2 and Pre-S1. The S-surface antigen accounts for about 80% or more of the total expressed surface antigen.

Interferon α and Lamivudin have been widely used for treating chronic hepatitis (C. L. Lai and P. C. Wu, *H.K.M.J.* 3: 289-296, 1997). However, interferon α shows high toxicity in spite of its immune response against in vivo virus. On the other hand, Lamivudin acting as a nucleic acid derivative shows anti-viral activity by way of inhibiting DNA polymerase. A lamivudin formulation for oral administration exhibits high therapeutic effect, but when it is taken for a long time, there is a high risk of inducing a mutant resistant to Lamivudin (Daryl T. Y. Lau et al, *Hepatology* 32: 828-834, 2000). Further, an anti-HBV polyclonal antibody isolated from human serum has been used for preventing HBV infection from liver transplantation and vertical transmission. However, this antibody also has problems in that it shows low antigen specificity and must be isolated from human blood.

A method employing a mouse monoclonal antibody against HBV surface antigen has been recently developed so as to solve the problems mentioned above, but a human antibody is formed against the mouse monoclonal antibody when used for a long time (Dimaggio J. J., et al., *Cancer Chemother. Biol. Response Modif* 11: 177-203, 1990).

To overcome the undesirable properties of mouse monoclonal antibodies, a humanized antibody has been developed by replacing the framework regions except for the antigen-binding site with regions of a human antibody. A method currently used for preparing such a humanized antibody comprises the steps of selecting a gene encoding the human antibody showing the closest sequence similarity to the mouse antibody and replacing only the complementarity determining region (CDR) of the mouse antibody with that of the human antibody by way of a CDR grafting method. The humanized antibody has the advantage of reducing the in vivo immune response (Riechmann et al., *Nature* 332: 323, 1988; Nakatani et al., *Protein Engineering* 7: 435, 1994). However, when only the CDR is grafted on the human antibody, its selectivity and reactivity are often compromised (Carter P., et al., *Proc. Natl. Acad. Sci. USA* 89: 4285-4289, 1992).

The present inventors have endeavored to overcome such problems of the conventional humanized antibody, and developed a novel humanized antibody against S-surface antigen of HBV which maintains antibody specificity of a mouse monoclonal antibody against HBV S-surface antigen while minimizing the immune response to the mouse monoclonal antibody.

SUMMARY OF THE INVENTION

Accordingly, it is an object of the present invention to provide a humanized antibody against S-surface antigen of HBV and a method for the preparation thereof.

It is another object of the present invention to provide a pharmaceutical composition for treating diseases relating to HBV comprising the humanized antibody as an effective ingredient.

In accordance with one aspect of the present invention, there is provided a humanized antibody against S-surface antigen of HBV which comprises a) a heavy chain variable region having the amino acid sequences of SEQ ID NOs: 38 to 40 at a complementarity determining region (CDR);

b) a light chain variable region having the amino acid sequences of SEQ ID NOs: 41 to 43 at the CDR;

c) a heavy chain constant region identical to that of a human antibody; and d) a light chain constant region identical to that of a human antibody.

BRIEF DESCRIPTION OF THE DRAWINGS

The above and other objects and features of the present invention will become apparent from the following description of the invention, when taken in conjunction with the accompanying drawings, which respectively show:

FIG. 1: the heavy chain amino acid sequences of the mouse monoclonal antibody A9-11-5 against HBV S-surface antigen, humanized antibody HFW141 and human antibody subgroup 2 (Hh2);

FIG. 2: the light chain amino acid sequences of the mouse monoclonal antibody A9-11-5 against HBV S-surface antigen, humanized antibodies LFW22-31 and LFW22-312 and human antibody subgroup 7 (hV7);

Lane 3: YHB-1110-15

Figure 6:
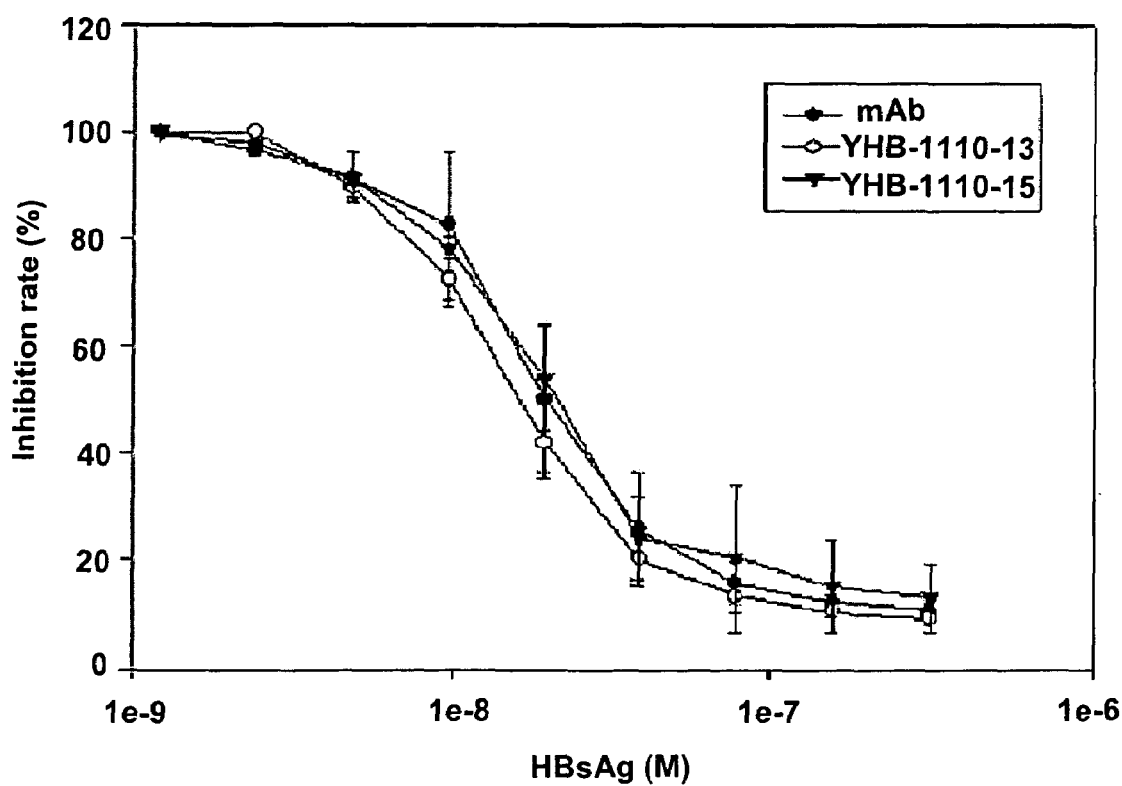

FIG. 6: antigen-binding affinities of humanized antibodies YH1110-13 and YHB1110-15 against HBV S-surface antigen.

DETAILED DESCRIPTION OF THE INVENTION

The present invention discloses a humanized antibody whose antigen-binding site, a complementarity determining region (CDR) in the heavy chain variable region or the light chain variable region is derived from a mouse monoclonal antibody, and the framework regions of the antibody molecule are derived from a human antibody. Preferably, the humanized antibody exhibits an antigen-binding affinity (Ka) ranging from $7 \times 10^7$ M$^{-1}$ to $1 \times 10^8$ M$^{-1}$.

The humanized antibody of the present invention can be prepared from the mouse monoclonal antibody A9-11-5 (Accession NOs: KCTC 18020P and KCTC 18021P) according to a CDR grafting method, wherein the heavy chain variable region of the mouse monoclonal antibody A9-11-5 comprises three CDR regions of SEQ ID NOs: 38 to 40, and the light chain variable region, three CDR regions of SEQ ID NOs: 41 to 43.

First, the amino acid sequences of the light chain and heavy chain variable regions of mouse monoclonal antibody A9-11-5 are compared with human sequences in the GenBank database, and selected are the human heavy chain variable region subgroup 2 (Hh2) as defined by Kabat having the greatest sequence similarity to the mouse antibody A9-11-5 heavy chain and the human light chain variable region subgroup 7 (hV7) or V3 of human Ig lambda germline V genes of GenBank Ig blast that has the most similarity to the mouse antibody A9-11-5 light chain (Kawasaki K., et al., *Genome Res.*, 7: 250-261, 1997).

The genes encoding the humanized antibody heavy chain and light chain can be amplified by using the so-selected human genes as templates. In this procedure, each of the nucleotide sequences encoding the humanized antibody heavy chain and light chain may be modified based on the information of well-known genetic studies and antibody structural analyses. Further, if certain nucleotide sequences of the mouse monoclonal antibody encode amino acid residues affect the antigen-binding affinity or are important for the antibody structure, they are preserved without replacing with sequences (Kabat E. A., et al., *D.H.H.S.* 91: 3242, 1991; Chothia C., et al., *Nature* 342: 877-883, 1989; Gary M., et al., *Protein Engineering* 7: 805-814, 1994; Linda Harris and Bajorath, J., *Protein Science* 4: 306-310, 1995).

A gene encoding the heavy chain variable region of the humanized antibody may be prepared by replacing the framework regions except for the antigen-binding site in the heavy chain variable region of the mouse monoclonal antibody A9-11-5 specifically recognizing HBV S-surface antigen with the heavy chain subgroup 2 (Hh2) of a human antibody. Such a gene encoding the heavy chain variable region of the humanized antibody can be prepared by the steps of: designing primers for humanizing the mouse monoclonal antibody using the gene encoding the mouse monoclonal antibody A9-11-5 heavy chain as a template; performing PCR (polymerase chain reaction) using the corresponding primers; and ligating the so-amplified PCR products to each other using restriction enzymes and DNA ligase. The gene encoding the heavy chain variable region of the humanized antibody thus prepared has been designated HFW141 (SEQ ID NO: 32) which encodes the polypeptide having the amino acid sequence of SEQ ID NO: 35 (see FIG. 1).

In order to prepare a gene encoding the full-length heavy chain of the humanized antibody including the gene encoding the humanized heavy chain variable region, gene HFW141 is inserted into a PCR vector to prepare expression vector pCR-HFW141. At this time, it is preferred to insert the Kozak sequence (Kozak, M. *Nuc. Acids Res.* 15: 8125-8148, 1987) in front of the heavy chain leader sequence of the humanized antibody, and replace some codons of the heavy chain leader sequence by other codons showing high frequency of use in animal cells, which results in increasing the expression efficiency of the heavy chain variable region of the humanized antibody (SEQ ID NO: 1). The gene fragment encoding the heavy chain variable region of the humanized antibody is isolated from expression vector pCR-HFW141, and inserted into expression vector pHAB-HC (Accession NO: KCTC 10229BP; Korean Patent Laid-Open NO: 2004-12266) containing the gene encoding the heavy chain constant region of the human antibody, to obtain expression vector of the humanized antibody heavy chain. Expression vector thus prepared has been designated pHAB-HFW141 HF (Accession NO: KCTC 10533BP). The gene encoding the full-length heavy chain of the humanized antibody can be isolated from the heavy chain expression vector pHAB-HFW141 HF and has been designated HFW141 HF.

The *E. coli* TOP10F' transformant transformed with humanized heavy chain expression vector pHAB-HFW141 HF was deposited on Oct. 29, 2003 with the Korean Collection for Type Cultures (KCTC)(Address: Korea Research Institute of Bioscience and Biotechnology (KRIBB), #52, Oun-dong, Yusong-ku, Taejon, 305-333, Republic of Korea) under the accession number KCTC 10533BP, in accordance with the terms of Budapest Treaty on the International Recognition of the Deposit of Microorganisms for the Purpose of Patent Procedure.

A gene encoding the light chain variable region of the humanized antibody may be prepared by replacing the framework regions except for the antigen-binding site in the light chain variable region of mouse monoclonal antibody A9-11-5 specifically recognizing HBV S-surface antigen with the light chain subgroup 7 (hV7) or the light chain lambda germline V3 of a human antibody. Such a gene encoding the light chain variable region of the humanized antibody can be prepared by the steps of: designing primers for humanizing the mouse monoclonal antibody using the gene encoding the mouse monoclonal antibody A9-11-5 light chain as a template; performing PCR using the corresponding primers; and ligating the so-amplified PCR products to each other using restriction enzymes and DNA ligase. Each of the genes encoding the light chain variable region of the humanized antibody thus prepared has been designated LFW22-31 (SEQ ID NO: 33) and LFW22-312 (SEQ ID NO: 34) that encode the polypeptides having the nucleotide sequences of SEQ ID NOs: 36 and 37, respectively (see FIG. 2).

In order to prepare a gene encoding the full-length light chain of the humanized antibody including the gene encoding the humanized light chain variable region, gene LFW22-31 or LFW22-312 is inserted into a PCR vector to prepare expression vectors pCR-LFW22-31 or pCR-LFW22-312. At this time, it is preferred to insert the Kozak sequence (Kozak, M. *Nuc. Acids Res.* 15: 8125-8148, 1987) in front of the light chain leader sequence of the humanized antibody, and replace some codons of the light chain leader sequence by other codons showing high frequency of use in animal cells, which results in increasing the expression efficiency of the light chain variable region of the humanized antibody (SEQ ID NO: 13). The gene fragment encoding the light chain variable region of the humanized antibody is isolated from expression vector pCR-LFW22-31 or pCR-LFW22-312, and inserted into expression vector pHAB-LC (Accession NO: KCTC 10231BP; Korean Patent Laid-Open NO: 2004-12267) containing the gene encoding the light chain constant region of the human antibody, to obtain an expression vector of the humanized antibody light chain. Each of the so-constructed expression vectors has been designated pHAB-LFW22-31 LF (Accession NO: KCTC 10532BP) and pHAB-LFW22-312 LF (Accession NO: KCTC 10553BP). The genes encoding the full-length humanized light chain can be isolated from the light chain expression vectors pHAB-LFW22-31 LF and pHAB-LFW22-312 LF, and have been designated LFW22-31 LF and LFW22-312 LF, respectively.

E. coli TOP10F' transformants transformed with each of the humanized light chain expression vectors pHAB LFW22-31 LF and pHAB LFW22-312 LF were deposited on Oct. 29, 2003 and Nov. 25, 2003 with the Korean Collection for Type Cultures (KCTC)(Address: Korea Research Institute of Bioscience and Biotechnology (KRIBB), #52, Oun-dong, Yusong-ku, Taejon, 305-333, Republic of Korea) under the accession numbers KCTC 10532BP and 10553BP, respectively, in accordance with the terms of Budapest Treaty on the International Recognition of the Deposit of Microorganisms for the Purpose of Patent Procedure.

CHO cell lines may be transformed with humanized heavy chain expression vector pHAB-HFW141 HF and humanized light chain expression vector pHAB-LFW22-31 LF by using an appropriate transformation solution such as GeneP-ORTER, to obtain a trasnformant producing the humanized antibody specifically recognizing HBV S-surface antigen, and the transformant has been designated CHO-YHB1110-13. Further, another transformant may be prepared by using humanized heavy chain expression vector pHAB-HFW141 HF and humanized light chain expression vector pHAB-LFW22-312 LF according to the same method as described above, and has been designated CHO-YHB1110-15.

To purify the humanized antibody of the present invention from the transformant cell lines, the transformant CHO-YHB1110-13 or CHO-YHB 1110-15 may be cultured in an appropriate culture medium, and the culture supernatant may be subjected to column chromatography using Protein-A (Amersham Bioscience, Sweden) or goat anti-human immunoglobulin G (Zymed Laboratories Inc., USA). The humanized antibodies thus purified have been designated YHB1110-13 and YHB1110-15, respectively.

Humanized antibodies YHB1110-13 and YHB1110-15 specifically recognizing HBV S-surface antigen show antigen-binding affinities ranging from $6 \times 10^7$ to $5 \times 10^8$ $M^{-1}$, which demonstrates that the humanized antibodies of the present invention maintain an antigen-binding activity similar to the previous reported mouse monoclonal antibody, but show significantly decreased immunogenecity, and therefore, can be effectively used for treating HBV-relating diseases without encountering adverse side-effects.

For this purpose, the humanized antibody of the present invention can be used as an effective ingredient in a pharmaceutical composition to treat HBV-relating diseases. The pharmaceutical composition can be formulated as an oral or non-oral dosage form, for immediate or extended release. The composition can comprise inactive ingredients ordinarily used in pharmaceutical preparation such as diluents, fillers, disintegrants, sweeteners, lubricants and flavors. The pharmaceutical composition is preferably formulated for intravenous administration, either by bolus injection or sustained drip, or for release from an implanted capsule. A typical formulation for intravenous administration utilizes physiological saline as a diluent.

Formulation of antibodies for therapeutic administration is considered known in the art.

The dose for a patient population depends upon the specific antibody used, body weight, age, gender, state of health, diet, administration time and formulation of the composition, route of administration, and the disease to be treated. A typical dose is from 0.01 mg/kg/day to 1,000 mg/kg/day. More typically the dose is from 0.1 mg/kg/day to 10 mg/kg/day.

The composition of the present invention can also include printed matter that describes clinical indications for which the antibodies can be administered as a therapeutic agent, dosage amounts and schedules, and/or contraindications for administration of the antibodies of the invention to a patient.

The following Examples are intended to further illustrate the present invention without limiting its scope.

EXAMPLE 1

Construction of a Gene Encoding a Heavy Chain Variable Region of a Humanized Antibody PCR was conducted using a gene encoding the heavy chain variable region of the mouse monoclonal antibody A9-11-5 (Accession NOs: KCTC 18020P and KCTC 18021P) against HBV S-surface antigen as a template and a primer pair of SEQ ID NOs: 1 and 12, to amplify gene A encoding the heavy chain variable region of the humanized antibody carrying a leader sequence. The amplified PCR product was electrophoresed on an agarose gel and recovered from the gel using a QIAgel extraction kit (Qiagen, USA).

Gene A thus purified was subjected to PCR with a primer pair of SEQ ID NOs: 1 and 3 or SEQ ID NOs: 2 and 12. Each of the amplified PCR products was digested with StuI (BioLabs Inc., USA) at 37° C. for 2 hrs, and then, treated with T4 DNA ligase (BioLabs Inc, USA) at room temperature for 1 hr, to prepare gene B encoding the heavy chain variable region.

PCR was conducted using gene B as a template and a primer pair of SEQ ID NOs: 4 and 12 or SEQ ID NOs: 1 and 5. Each of the amplified PCR products was digested with PstI (BioLabs Inc., USA) at 37° C. for 2 hrs, and then, treated with T4 DNA ligase (BioLabs Inc., USA) at room temperature for 1 hr, to prepare gene C encoding the heavy chain variable region.

In the same manner as described above, gene C was subjected to PCR with a primer pair of SEQ ID NOs: 6 and 12 or SEQ ID NOs: 1 and 7, and the PCR products thus amplified were treated with SalI (BioLabs Inc., USA), to obtain gene D encoding the heavy chain variable region. Gene D was subjected to PCR with a primer pair of SEQ ID NOs: 8 and 12 or SEQ ID NOs: 1 and 9, and the PCR products thus amplified were treated with DraI (BioLabs Inc., USA), to obtain Gene E encoding the heavy chain variable region. PCR was conducted using Gene E as a template and a primer pair of SEQ ID NOs: 10 and 12 or SEQ ID NOs: 1 and 11. Each of the PCR products was digested with XbaI (BioLabs Inc., USA) at 37° C. for 2 hrs, and then, treated with T4 DNA ligase (BioLabs Inc., USA) at room temperature for 1 hr, to obtain gene A9V7FW42HV encoding the heavy chain variable region.

PCR was conducted using gene A9V7FW42HV as a template and a primer pair of SEQ ID NOs: 23 and 25 or SEQ ID NO: 1 and 24 according to the condition described in Table 1. Two PCR products were mixed at an equal molar ratio, and the mixture was subjected to overlapping PCR with a primer pair of SEQ ID NOs: 1 and 25. The PCR thermal cycle was repeated 30 times, each cycle being composed of: 95° C. for 2 min, 58° C. for 2 min and 72° C. for 2 min. The final gene encoding the heavy chain variable region of the humanized antibody thus amplified has been designated HFW141.

The nucleotide sequences of the primers and reaction conditions employed in each PCR reaction are shown in Table 1.

Each PCR reaction was conducted under the following conditions of 30 cycles as shown in Table 1 after initial denaturation of 5 min at 95° C., and final extension of 10 min at 72° C.

TABLE 1

| Primer pair | Gene | PCR condition | | |
|---|---|---|---|---|
| | | Denature | Annealing | Extension |
| SEQ ID NOs: 1 and 12 | A | 94° C., 1.5 min | 55° C., 2 min | 72° C., 3 min |
| SEQ ID NOs: 1 and 3 | B | 94° C., 1.5 min | 50° C., 2 min | 72° C., 2.5 min |
| SEQ ID NOs: 2 and 12 | | 94° C., 1.5 min | 50° C., 2 min | 72° C., 2.5 min |
| SEQ ID NOs: 4 and 12 | C | 94° C., 1.5 min | 55° C., 2 min | 72° C., 2.5 min |
| SEQ ID NOs: 1 and 5 | | 94° C., 1.5 min | 55° C., 2 min | 72° C., 2.5 min |
| SEQ ID NOs: 6 and 12 | D | 94° C., 1.5 min | 55° C., 2 min | 72° C., 2.5 min |
| SEQ ID NOs: 1 and 7 | | 94° C., 1.5 min | 55° C., 2 min | 72° C., 2.5 min |
| SEQ ID NOs: 8 and 12 | E | 94° C., 1.5 min | 55° C., 2 min | 72° C., 2.5 min |
| SEQ ID NOs: 1 and 9 | | 94° C., 1.5 min | 55° C., 2 min | 72° C., 2.5 min |
| SEQ ID NOs: 10 and 12 | A9V7FW42HV | 94° C., 1.5 min | 55° C., 2 min | 72° C., 2.5 min |
| SEQ ID NOs: 1 and 11 | | 94° C., 1.5 min | 55° C., 2 min | 72° C., 2.5 min |
| SEQ ID NOs: 23 and 25 | HFW141 | 95° C., 1 min | 55° C., 1.5 min | 72° C., 1.5 min |
| SEQ ID NOs: 1 and 24 | | 95° C., 1 min | 55° C., 1.5 min | 72° C., 1.5 min |

EXAMPLE 2

Construction of a Full-Length Heavy Chain Gene of a Humanized Antibody and an Expression Vector Thereof In order to improve the expression efficiency of the gene encoding the heavy chain variable region of the humanized antibody, primers were so designed as to insert the Kozak sequence (Kozak, M. *Nuc. Acids Res.* 15: 8125-8148, 1987) in front of the heavy chain leader sequence of the humanized antibody and replace the codon TTA encoding the $4^{th}$ amino acid, leucine, of the heavy chain leader sequence with CTG preferable used in animal cells. The modified heavy chain leader sequence of the humanized antibody is shown in Table 2.

TABLE 2

| Primer | Sequence |
|---|---|
| Humanized heavy chain leader sequence (SEQ ID NO:1) | CACC ATG GCT GTC CTG TTC CTG CTC CTC TGC CTG |

Gene HFW141 encoding the heavy chain variable region of the humanized antibody prepared in Example 1 was cloned into a PCR vector, to obtain expression vector pCR-HFW141.

Further, in order to construct the gene encoding the humanized full-length heavy chain, expression vector pHAB-HC (KCTC 10229BP, Korean Patent Laid-Open NO: 2004-12266) containing the gene encoding the heavy chain constant region of the human antibody was employed. First, in order to insert gene HFW141 encoding the heavy chain variable region of the humanized antibody into expression vector pHAB-HC, expression vector pCR-HFW141 was treated with HindIII/ApaI (BioLabs, Inc., USA) at 37° C. for 2 hrs, electrophoresed on a 1.5% agarose gel and stained with etidium bromide (EtBr), to obtain an about 450 bp fragment of the gene.

In the same manner as described above, expression vector pHAB-HC was treated with HindIII/ApaI, to obtain an about 6.5 kb fragment of the vector. After then, each of the gene fragments was recovered from the gels using a QIAgel extraction kit (Qiagen, USA), treated with T4 DNA ligase (BioLabs, Inc., USA) at 16° C. overnight, and transformed into *E. coli* TOP10F', to obtain a transformant. The transformant was cultured in an LB medium supplemented with 100 μg/ml of ampicillin overnight, and plasmids were isolated from the culture medium. The isolated plasmids were treated with HindIII/ApaI and subjected to agarose gel electrophoresis, to obtain an about 1.4 kb full-length heavy chain of the humanized antibody.

Figure 3:
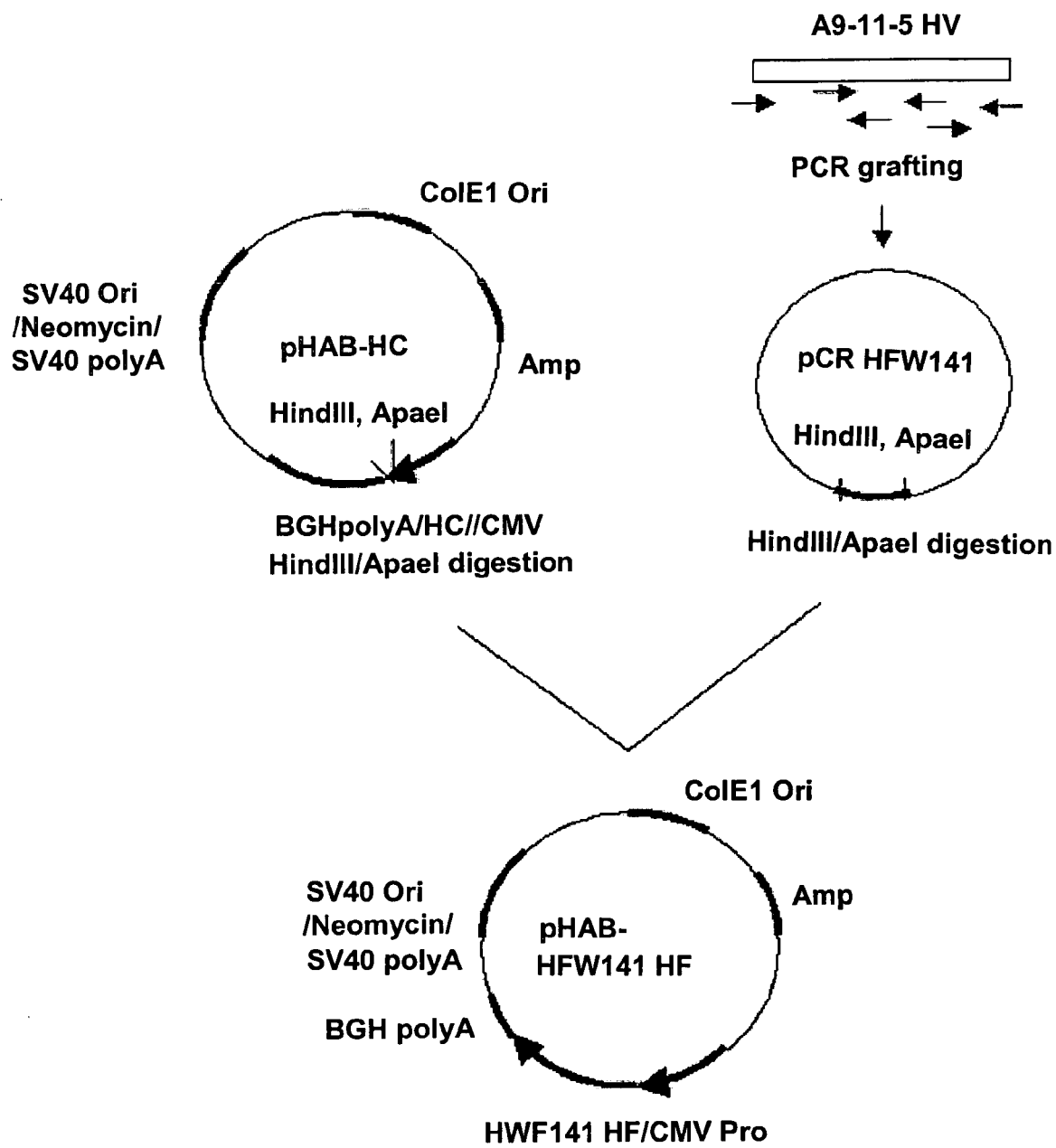
FIG. 3: the procedure for constructing humanized antibody heavy chain expression vector pHAB-HFW141 HF.

The full-length heavy chain of the humanized antibody thus prepared was designated HFW141 HF. Further, the heavy chain expression vector of the humanized antibody inserted with the full-length heavy chain HFW141 HF of the humanized antibody was designated pHAB-HFW141 HF (FIG. 3), and transformed into *E. coli* TOP10F', to obtain a transformant, which was deposited on Oct. 29, 2003 with the Korean Collection for Type Cultures (KCTC)(Address: Korea Research Institute of Bioscience and Biotechnology (KRIBB), #52, Oun-dong, Yusong-ku, Taejon, 305-333, Republic of Korea) under the accession number KCTC 10533BP.

EXAMPLE 3

Construction of a Gene Encoding a Light Chain Variable Region of a Humanized Antibody PCR was conducted using the gene encoding the light chain variable region of mouse monoclonal antibody A9-11-5 specifically recognizing HBV S-surface antigen as a template and a primer pair of SEQ ID NOs: 13 and 22, to amplify gene A' encoding the light chain variable region containing a leader sequence. Gene A' was subjected to agarose gel electrophoresis and EtBr staining, and then, recovered from the gel using a QIAgel extraction kit.

Purified gene A' was subjected to PCR with a primer pair of SEQ ID NOs: 14 and 22 or a primer pair of SEQ ID NOs: 13 and 15. The amplified PCR product was digested with KpnI (BioLabs, Inc., USA) at 37° C. for 2 hrs, and treated with T4 DNA ligase (BioLabs, Inc., USA) at room temperature for 1 hr, to obtain gene B' encoding the light chain variable region.

PCR was carried out using gene B' as a template and a primer pair of SEQ ID NOs: 16 and 22 or a primer pair of SEQ ID NOs: 13 and 17. The amplified PCR product was digested with MscI (BioLabs, Inc., USA) at 37° C. for 2 hrs, and treated with T4 DNA ligase (BioLabs, Inc., USA) at room temperature for 1 hr, to obtain gene C' encoding the light chain variable region.

In the same manner as described above, gene C' was subjected to PCR with a primer pair of SEQ ID NOs: 18 and 22 or a primer pair of SEQ ID NOs: 13 and 19, and PCR products thus amplified were digested with ApaLI (BioLabs, Inc., USA), to obtain gene D' encoding the light chain variable region.

Further, after PCR was conducted using gene D' as a template and a primer pair of SEQ ID NOs: 20 and 22 or a primer pair of SEQ ID NOs: 13 and 21, the PCR products thus amplified were digested with SmaI (BioLabs, Inc., USA) and treated with T4 DNA ligase (BioLabs, Inc., USA) at room temperature for 1 hr, to obtain gene A9V7LV encoding the light chain variable region.

PCR was conducted using gene A9V7LV as a template and a primer pair of SEQ ID NOs: 26 and 22 or SEQ ID NO: 13 and 27 according to the condition described in Table 3. Two PCR products were mixed at an equal molar ratio, and the mixture was subjected to overlapping PCR with a primer pair of SEQ ID NOs: 13 and 22. The PCR thermal cycle was repeated 30 times, each cycle being composed of: 95° C. for 2 min, 58° C. for 2 min and 72° C. for 2 min. The gene encoding the light chain variable region of the humanized antibody thus amplified has been designated LFW22.

In the same manner as described above, PCR was conducted using gene LFW22 as a template and a primer pair of SEQ ID NOs: 28 and 22 or SEQ ID NO: 13 and 29 according to the condition described in Table 3. Two PCR products were mixed at an equal molar ratio, and the mixture was subjected to overlapping PCR with a primer pair of SEQ ID NOs: 13 and 22. The PCR thermal cycle was repeated 30 times, each cycle being composed of: 95° C. for 2 min, 58° C. for 2 min and 72° C. for 2 min. The final gene encoding the light chain variable region of the humanized antibody thus amplified has been designated LFW22-31.

In the same manner as described above, PCR was conducted using gene LFW22-31 as a template and a primer pair of SEQ ID NOs: 30 and 22 or SEQ ID NO: 13 and 31 according to the condition described in Table 3. Two PCR products were mixed at an equal molar ratio, and the mixture was subjected to overlapping PCR with a primer pair of SEQ ID NOs: 13 and 22. The PCR thermal cycle was repeated 30 times, each cycle being composed of: 95° C. for 2 min, 58° C. for 2 min and 72° C. for 2 min. The final gene encoding the light chain variable region of the humanized antibody thus amplified has been designated LFW22-312.

The nucleotide sequences of the primers and PCR conditions employed in the above PCR reactions are described in the following Table 3.

Each of the PCR reactions was conducted under the conditions of 30 cycles as shown in Table 3 after initial denaturation of 5 min at 95° C., and final extension of 10 minutes at 72° C.

TABLE 3

| Primer pair | Gene | PCR conditions | | |
|---|---|---|---|---|
| | | Denature | Annealing | Extension |
| SEQ ID NOs: 13 and 22 | A' | 94° C., 1.5 min | 55° C., 2 min | 72° C., 3 min |
| SEQ ID NOs: 14 and 22 | B' | 94° C., 1.5 min | 55° C., 2 min | 72° C., 3 min |
| SEQ ID NOs: 13 and 15 | | 94° C., 1.5 min | 55° C., 2 min | 72° C., 3 min |
| SEQ ID NOs: 16 and 22 | C' | 94° C., 1.5 min | 49° C., 2 min | 72° C., 3 min |
| SEQ ID NOs: 13 and 17 | | 94° C., 1.5 min | 50° C., 2 min | 72° C., 3 min |
| SEQ ID NOs: 18 and 22 | D' | 94° C., 1.5 min | 55° C., 2 min | 72° C., 3 min |
| SEQ ID NOs: 13 and 19 | | 94° C., 1.5 min | 55° C., 2 min | 72° C., 3 min |
| SEQ ID NOs: 20 and 22 | A9V7LV | 94° C., 1.5 min | 55° C., 2 min | 72° C., 3 min |
| SEQ ID NOs: 13 and 21 | | 94° C., 1.5 min | 55° C., 2 min | 72° C., 3 min |
| SEQ ID NOs: 26 and 22 | LFW22 | 95° C., 1 min | 55° C., 2 min | 72° C., 1.5 min |
| SEQ ID NOs: 13 and 27 | | 95° C., 1 min | 50° C., 2 min | 72° C., 1.5 min |
| SEQ ID NOs: 28 and 22 | LFW22-31 | 95° C., 1 min | 55° C., 1.5 min | 72° C., 1.5 min |
| SEQ ID NOs: 13 and 29 | | 95° C., 1 min | 55° C., 1.5 min | 72° C., 1.5 min |
| SEQ ID NOs: 30 and 22 | LFW22-312 | 95° C., 1 min | 55° C., 1.5 min | 72° C., 1.5 min |
| SEQ ID NOs: 13 and 31 | | 95° C., 1 min | 55° C., 1.5 min | 72° C., 1.5 min |

EXAMPLE 4

Construction of a Full-Length Light Chain Gene of a Humanized Antibody and an Expression Vector Thereof In order to enhance the expression of the gene encoding the light chain variable region of the humanized antibody, primers were so designed as to insert the Kozak sequence in front of the light chain leader sequence of the humanized antibody (Kozak, M. *Nuc. Acids Res.*, 15: 8125-8148, 1987), and replace the $8^{th}$ amino acid, phenylalanine, in the nucleotide sequence of the gene encoding the light chain leader sequence was replaced with leucine preferable used in animal cells. Further, CTT encoding the $6^{th}$ leucine was replaced with CTG and ATA encoding the $7^{th}$ isoleucine, with ATC. The modified light chain leader sequence of the humanized antibody is shown in Table 4.

TABLE 4

| Primer | Sequence |
|---|---|
| Humanized light chain leader sequence (SEQ ID NO:13) | CACC ATG GCC TGG ATT TCA CTG ATC CTC TCT CTC CTG |

Gene LFW22-31 encoding the light chain variable region of the humanized antibody prepared in Example 3 was inserted into a PCR vector, to obtain expression vector pCR-LFW22-31.

Further, in order to prepare the full-length light chain of the humanized antibody, expression vector pHAB-LC (KCTC 10231BP, Korean Laid-Open NO: 2004-12267) containing the gene encoding the light chain constant region of the human antibody was employed.

First, in order to insert gene LFW22-31 encoding the light chain variable region of the humanized antibody into expression vector pHAB-LC, expression vector pCR-LFW22-31 was treated with HindIII/AvrII at 37° C. for 2 hrs, and electrophoresed on a 1.5% agarose gel and stained with EtBr, to obtain an about 400 bp fragment of the gene.

In the same manner as described above, expression vector pHAB-LC was treated with HindIII/AvrII to obtain an about 5.6 kb fragment of the vector. Each of the gene fragments was recovered from the gels using a QIAgel extraction kit (Qiagen, USA), treated with T4 DNA ligase (BioLabs, Inc., USA) at 16° C. overnight, and then, transformed into $E.$ $coli$ TOP10F' to obtain a transformant. The transformant was cultured in an LB medium supplemented with 100 μg/ml of ampicillin overnight, and a plasmid was isolated from the culture solution. The plasmid was treated with HindIII/NotI (BioLabs, Inc., USA) and subjected to agarose gel electrophoresis, to obtain an about 0.7 kb full-length light chain of the humanized antibody.

Figure 4:
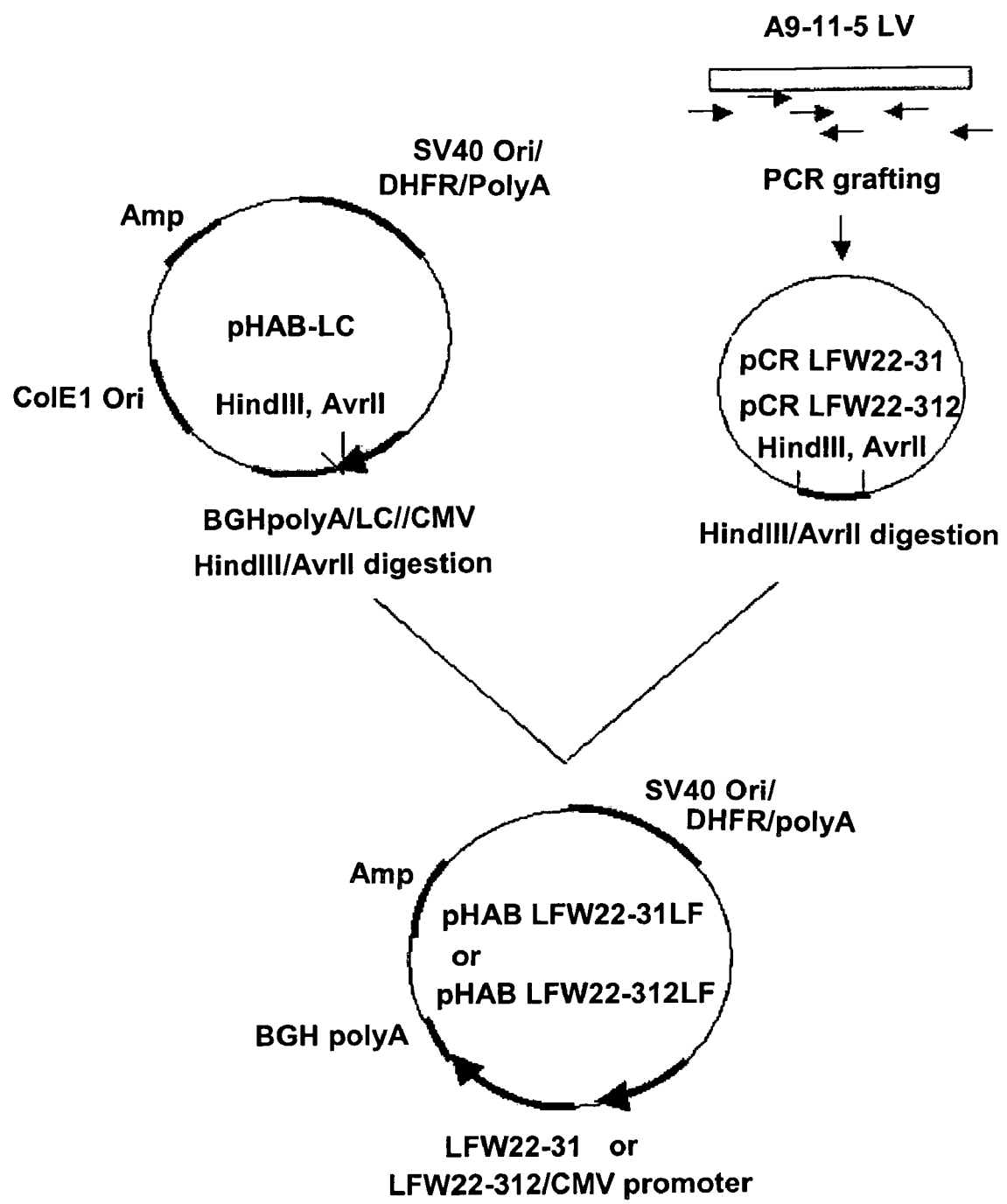
FIG. 4: the procedure for constructing humanized antibody light chain expression vectors pHAB-LFW22-31 LF and pHAB-LFW22-312 LF.

The so-prepared gene encoding the full-length light chain of the humanized antibody was designated LFW22-31 LF. Further, the light chain expression vector of the humanized antibody containing the gene LFW22-31 LF was designated pHAB LFW22-31 LF (FIG. 4), and transformed into $E.$ $coli$ TOP10F' to obtain a transformant, which was deposited on Oct. 29, 2003 with the Korean Collection for Type Cultures (KCTC)(Address: Korea Research Institute of Bioscience and Biotechnology (KRIBB), #52, Oun-dong, Yusong-ku, Taejon, 305-333, Republic of Korea) under the accession number KCTC 10532BP.

Another full-length light chain of the humanized antibody was prepared by using gene LFW22-312 according to the same method as described above, and was designated LFW22-312 LF. Further, the light chain expression vector of the humanized antibody containing gene LFW22-312 LF was designated pHAB LFW22-312 LF (FIG. 4), and transformed into $E.$ $coli$ TOP10F' to obtain a transformant, which was deposited on Nov. 25, 2003 with the Korean Collection for Type Cultures (KCTC)(Address: Korea Research Institute of Bioscience and Biotechnology (KRIBB), #52, Oun-dong, Yusong-ku, Taejon, 305-333, Republic of Korea) under the accession number KCTC 10553BP.

EXAMPLE 5

Transformation of a Humanized Antibody into CHO Cell Lines

In order to measure the humanized antibody activity in animal cells, heavy chain expression vector pHAB-HFW141 HF prepared in Example 2 and light chain expression vector pHAB-LFW22-31 LF prepared in Example 4 were transformed into CHO cells (ATCC CRL-9096, USA).

First, CHO cells were cultured in a DMEM/F12 medium (JRH Inc., USA) supplemented with 1.5 g/l of sodium bicarbonate (Sigma, USA) and 10% heat inactivated FBS (Gibco BRL, USA) in a 37° C. humidified $CO_2$ incubator for 2 to 3 days. The culture solution was centrifuged at 1,200 rpm, room temperature (25° C.) for 5 min, to harvest a cell pellet. The cells were stained with 0.4% trypan blue (Gibco BRL, USA), and counted with a hematocytometer. The cells were transferred to a T-225 flask (or T-75 flask) in an amount of about $6 \times 10^6$ cells and subjected to sub-culture.

The sub-cultured CHO cells were allowed to proliferate until they occupied the flask's surface by as much as about 60 to 90%. 10 μg of the gene to be transformed and 40 μl of a GenePORTER solution (GTS, USA) for transformation were mixed with 5 ml of a DMEM/F12 (serum-free) medium. After the mixture was kept at room temperature for 10 to 45 min, the culture medium was removed therefrom, and the proliferated cells were cultured in a 37° C. humidified $CO_2$ incubator for about 3 to 5 hrs, to obtain a transformant, which was designated CHO-YHB1110-13.

Heavy chain expression vector pHAB-HFW141 HF prepared in Example 2 and light chain expression vector pHAB-LFW22-312 LF prepared in Example 4 were transformed into CHO cells to obtain another transformant according to the same method as described above, and the transformant was designated CHO-YHB1110-15.

EXAMPLE 6

Purification of a Humanized Antibody

The transformant CHO-YHB1110-13 cells obtained in Example 5 were inoculated into a T-75 flask containing a DMEM/F12 medium supplemented with 10% fetal bovine serum in an amount of $2 \times 10^6$ cells and incubated at 37° C. for 5 hrs. The culture solution was centrifuged to isolate a supernatant, and the supernatant was filtered, to obtain a cell-free culture solution.

In order to purify the humanized antibody from the culture solution, sepharose 4B columns conjugated with Protein-A (Pharmacia) and goat anti-human Immunoglobulin G (Zymed Laboratories Inc., USA) were employed. The culture supernatant was applied to Protein-A conjugated sepharose 4B column chromatography to bind the humanized antibody to Protein-A, and a glycine buffer (pH 2.5) was introduced into the column, to elute the humanized antibody. Then, the effluent was neutralized by mixing with 1 M Tris-Cl (pH 8.0) at a volume ratio of 1:10. The neutralized effluent was subjected to sepharose 4B column chromatography conjugated with goat anti-human IgG, to specifically capture the humanized antibody protein.

The humanized antibody was further purified according to the same method using the Protein-A column chromatography as described above and designated YHB1110-13.

Humanized antibody YHB1110-15 was purified by culturing the transformant CHO-YHB1110-15 prepared in Example 5 and purifying the antibody from the culture supernatant, according to the same method as described above.

Figure 5:
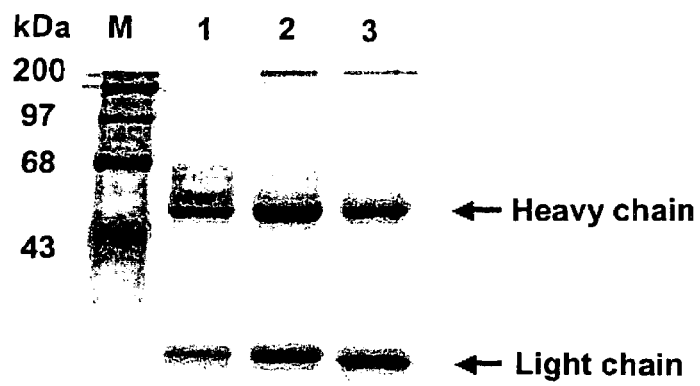
FIG. 5: the expression patterns of humanized antibodies YH1110-13 and YHB-1110-15 determined by SDS-PAGE analysis; and Lane 1: mouse antibody, Lane 2: YHB-1110-13

As a result of analyzing the purified humanized antibodies with SDS-PAGE, bands of about 50 kDa and about 25 kDa were observed, which were identified as the heavy chain and light chain of the humanized antibody, respectively (FIG. 5).

EXAMPLE 7

Measurement of Antigen-Binding Affinity of a Humanized Antibody Against HBV S-Surface Antigen The humanized antibodies purified in Example 6 were quantified with sandwich ELISA, and their antigen-binding activities were analyzed by using an S-surface antigen (International Enzyme Inc., USA) adr type. For antibody quantification, 100 ng of goat anti-human immunoglobulin G. A. M (Zymed Laboratories Inc., USA) was distributed into each well of a microplate (Dynatech Laboratories Inc., USA) and the well plate was kept at 4° C. overnight to coat it with the immunoglobulin. At this time, mouse monoclonal antibody A9-11-5 was used as a control.

In order to measure an antigen-binding affinity of the humanized antibody against HBV S-surface antigen, antigen solutions (100 µl each) having different concentrations ranging from $10^{-11}$ to $10^{-6}$ M were mixed with 5 ng of the mouse monoclonal antibody A9-11-5, humanized antibodies YHB1110-13 and YHB1110-15, respectively, and reacted at 37° C. for 1 hr. Each of the reactants was added to the well plate coated with 0.5 µg of the antigen and the well plate was kept at 37° C. for about 2 hrs. A goat anti-human polyclonal antibody (BioRad, USA) conjugated with horseradish peroxidase was diluted at a ratio of 1:1000 and 100 µl of the diluted antibody solution was added to each well. The well plate was kept at 37° C. for 1 hr. After the reaction was completed, the optical density of each well was measured using a horseradish peroxidase substrate kit (BioRad, USA).

Concentrations of the antibody bound to the antigen and the unbound antibody were calculated from the measured optical density, and antigen-binding affinity of the humanized antibodies were determined therefrom (Friguet, et al., *J. Immunol. Meth.* 77: 305-319, 1985). The results are shown in Table 5.

TABLE 5

| Antigen | Mouse antibody mA9-11-5 | Humanized antibody YHB1110-13 | Humanized antibody YHB1110-15 |
|---|---|---|---|
| Antigen-binding affinity (Ka) | $1 \times 10^8 \, M^{-1}$ | $1 \times 10^8 \, M^{-1}$ | $7 \times 10^7 \, M^{-1}$ |

As can be seen in Table 5, the antigen-binding affinities of humanized antibodies YHB1110-13 and YHB1110-15 were similar to that of mouse monoclonal antibody A9-11-5 (FIG. 6).

While the invention has been described with respect to the above specific embodiments, it should be recognized that various modifications and changes may be made to the invention by those skilled in the art which also fall within the scope of the invention as defined by the appended claims.

What is claimed is:

1. A humanized antibody against S-surface antigen of HBV which comprises
   a) a heavy chain variable region having the amino acid sequence of SEQ ID NO: 35;
   b) a light chain variable region having the amino acid sequences of SEQ ID NOs: 41 to 43 at the CDR;
   c) a heavy chain constant region identical to that of a human antibody; and
   d) a light chain constant region identical to that of a human antibody.

2. The humanized antibody of claim 1, wherein the heavy chain variable region is encoded by the polynucleotide having the nucleotide sequence of SEQ ID NO: 32.

3. A humanized antibody against S-surface antigen of HBV which comprises
   a) a heavy chain variable region having the amino acid sequences of SEQ ID NOs: 38 to 40 at the CDR;
   b) a light chain variable region having the amino acid sequence of SEQ ID NO: 36 or 37;
   c) a heavy chain constant region identical to that of a human antibody; and
   d) a light chain constant region identical to that of a human antibody.

4. The humanized antibody of claim 3, wherein the light chain variable region is encoded by the polynucleotide having the nucleotide sequence of SEQ ID NO: 33 or 34.

5. An expression vector of a heavy chain variable region of a humanized antibody specific for S-surface antigen of hepatitis B virus, which comprises the polynucleotide encoding the heavy chain variable region of SEQ ID NO: 35.

6. The expression vector of claim 5, which is pHAB-HFW141 HF.

7. An expression vector of a light chain variable region of a humanized antibody specific for S-surface antigen of hepatitis B virus, which comprises the polynucleotide encoding the light chain variable region of SEQ ID NO: 36 or 37.

8. The expression vector of claim 7, which is pHAB-LFW22-31 LF or pHAB-LFW22-312 LF.

9. An *E. coli* cell transformed with expression vector of claim 5 or claim 7.

10. The *E. coli* cell of claim 9 which is TOP10F'/pHAB-HFW141 HF (Accession NO: KCTC 10533 BP), TOP10F'/pHAB-LFW22-31 LF (Accession NO: KCTC 10532 BP) or TOP10F'/pHAB-LFW22-312 LF (Accession NO: KCTC 10553 BP).

11. A pharmaceutical composition comprising any one of the humanized antibodies of claims 1 to 4.

* * * * *

SEQUENCE LISTING

```
<160> NUMBER OF SEQ ID NOS: 43

<210> SEQ ID NO 1
<211> LENGTH: 34
<212> TYPE: DNA
<213> ORGANISM: Artificial Sequence
<220> FEATURE:
<223> OTHER INFORMATION: forward primer for heavy chain variable region

<400> SEQUENCE: 1
caccatggct gtcctgttcc tgctcctctg cctg                              34

<210> SEQ ID NO 2
<211> LENGTH: 45
<212> TYPE: DNA
<213> ORGANISM: Artificial Sequence
<220> FEATURE:
<223> OTHER INFORMATION: forward primer for heavy chain variable region

<400> SEQUENCE: 2
caggcctagt gaagccctca cagaccctgt ccctcacctg cacag                  45

<210> SEQ ID NO 3
<211> LENGTH: 33
<212> TYPE: DNA
<213> ORGANISM: Artificial Sequence
<220> FEATURE:
<223> OTHER INFORMATION: reverse primer for heavy chain variable region

<400> SEQUENCE: 3
taggcctggt ccgctctctt gcagctgcac ctg                               33

<210> SEQ ID NO 4
<211> LENGTH: 32
<212> TYPE: DNA
<213> ORGANISM: Artificial Sequence
<220> FEATURE:
<223> OTHER INFORMATION: forward primer for heavy chain variable region
```

<400> SEQUENCE: 4
gctgcagaca cagccgtgta ttattgtgcc ag                                    32

<210> SEQ ID NO 5
<211> LENGTH: 40
<212> TYPE: DNA
<213> ORGANISM: Artificial Sequence
<220> FEATURE:
<223> OTHER INFORMATION: reverse primer for heavy chain variable region

<400> SEQUENCE: 5
tctgcagcag tcacactgga cagtttcagg aaaacttggc                            40

<210> SEQ ID NO 6
<211> LENGTH: 39
<212> TYPE: DNA
<213> ORGANISM: Artificial Sequence
<220> FEATURE:
<223> OTHER INFORMATION: forward primer for heavy chain variable region

<400> SEQUENCE: 6
cgtcgacacc tccaagaacc aattctcact gaaactgtc                             39

<210> SEQ ID NO 7
<211> LENGTH: 29
<212> TYPE: DNA
<213> ORGANISM: Artificial Sequence
<220> FEATURE:
<223> OTHER INFORMATION: reverse primer for heavy chain variable region

<400> SEQUENCE: 7
tgtcgacgct gatggtcact ctggatatg                                        29

<210> SEQ ID NO 8
<211> LENGTH: 22
<212> TYPE: DNA
<213> ORGANISM: Artificial Sequence
<220> FEATURE:
<223> OTHER INFORMATION: forward primer for heavy chain variable region

<400> SEQUENCE: 8
ttctctttaa aactgtccag tg                                               22

<210> SEQ ID NO 9
<211> LENGTH: 40
<212> TYPE: DNA
<213> ORGANISM: Artificial Sequence
<220> FEATURE:
<223> OTHER INFORMATION: reverse primer for heavy chain variable region

<400> SEQUENCE: 9
ttttaaagag aattggttct tggaggtgtc cttgctgatg                            40

<210> SEQ ID NO 10
<211> LENGTH: 52
<212> TYPE: DNA
<213> ORGANISM: Artificial Sequence
<220> FEATURE:
<223> OTHER INFORMATION: forward primer for heavy chain variable region

<400> SEQUENCE: 10
atctagagtg accatcagca aggacacctc caagaaccaa gtttcactga aa              52

<210> SEQ ID NO 11
<211> LENGTH: 22
<212> TYPE: DNA
<213> ORGANISM: Artificial Sequence
<220> FEATURE:
<223> OTHER INFORMATION: reverse primer for heavy chain variable region

<400> SEQUENCE: 11
ctctagatat gaaagctgca tt                                              22

<210> SEQ ID NO 12
<211> LENGTH: 32
<212> TYPE: DNA
<213> ORGANISM: Artificial Sequence
<220> FEATURE:
<223> OTHER INFORMATION: reverse primer for heavy chain variable region

<400> SEQUENCE: 12
agagctcacg gtgaccgtgg tcccagcgcc cc                                   32

<210> SEQ ID NO 13
<211> LENGTH: 37
<212> TYPE: DNA
<213> ORGANISM: Artificial Sequence
<220> FEATURE:
<223> OTHER INFORMATION: forward primer for light chain variable region

<400> SEQUENCE: 13
caccatggcc tggatttcac tgatcctctc tctcctg                              37

<210> SEQ ID NO 14
<211> LENGTH: 25
<212> TYPE: DNA
<213> ORGANISM: Artificial Sequence
<220> FEATURE:
<223> OTHER INFORMATION: forward primer for light chain variable region

<400> SEQUENCE: 14
ggtggtaccg tcacactcac ttgtc                                           25

<210> SEQ ID NO 15
<211> LENGTH: 37
<212> TYPE: DNA
<213> ORGANISM: Artificial Sequence
<220> FEATURE:
<223> OTHER INFORMATION: reverse primer for light chain variable region

<400> SEQUENCE: 15
cggtaccgcc aggtgagacg gtgagtgaag gttcctg                              37

<210> SEQ ID NO 16
<211> LENGTH: 35
<212> TYPE: DNA
<213> ORGANISM: Artificial Sequence
<220> FEATURE:
<223> OTHER INFORMATION: forward primer for light chain variable region

<400> SEQUENCE: 16
ctggccaggc tcctagaact ctaatatatg atacc                                35

<210> SEQ ID NO 17
<211> LENGTH: 30
<212> TYPE: DNA
<213> ORGANISM: Artificial Sequence
<220> FEATURE:
<223> OTHER INFORMATION: reverse forward primer for light chain variable
      region

```
<400> SEQUENCE: 17
ctggccaggt ttctgttgga accagttggc                                          30

<210> SEQ ID NO 18
<211> LENGTH: 35
<212> TYPE: DNA
<213> ORGANISM: Artificial Sequence
<220> FEATURE:
<223> OTHER INFORMATION: forward primer for light chain variable region

<400> SEQUENCE: 18
ggtgcacagc ctgaagatgc agaatattat tgtgc                                    35

<210> SEQ ID NO 19
<211> LENGTH: 43
<212> TYPE: DNA
<213> ORGANISM: Artificial Sequence
<220> FEATURE:
<223> OTHER INFORMATION: reverse primer for light chain variable region

<400> SEQUENCE: 19
tgtgcaccga gtagggtgag ggcagccttg tttccgagca ggg                           43

<210> SEQ ID NO 20
<211> LENGTH: 25
<212> TYPE: DNA
<213> ORGANISM: Artificial Sequence
<220> FEATURE:
<223> OTHER INFORMATION: forward primer for light chain variable region

<400> SEQUENCE: 20
tcccgggtgt tcctgacaga ttctc                                               25

<210> SEQ ID NO 21
<211> LENGTH: 24
<212> TYPE: DNA
<213> ORGANISM: Artificial Sequence
<220> FEATURE:
<223> OTHER INFORMATION: reverse primer for light chain variable region

<400> SEQUENCE: 21
acccgggact cggttgttgg tatc                                                24

<210> SEQ ID NO 22
<211> LENGTH: 32
<212> TYPE: DNA
<213> ORGANISM: Artificial Sequence
<220> FEATURE:
<223> OTHER INFORMATION: reverse primer for light chain variable region

<400> SEQUENCE: 22
cccaagctta gctcttcagt ggagggtgga aa                                       32

<210> SEQ ID NO 23
<211> LENGTH: 21
<212> TYPE: DNA
<213> ORGANISM: Artificial Sequence
<220> FEATURE:
<223> OTHER INFORMATION: forward primer for heavy chain variable region

<400> SEQUENCE: 23
gctgaaacag agcggaccag g                                                   21
```

```
<210> SEQ ID NO 24
<211> LENGTH: 23
<212> TYPE: DNA
<213> ORGANISM: Artificial Sequence
<220> FEATURE:
<223> OTHER INFORMATION: reverse primer for heavy chain variable region

<400> SEQUENCE: 24
gcctggtccg ctctgtttca gct                                              23

<210> SEQ ID NO 25
<211> LENGTH: 34
<212> TYPE: DNA
<213> ORGANISM: Artificial Sequence
<220> FEATURE:
<223> OTHER INFORMATION: reverse primer for heavy chain variable region

<400> SEQUENCE: 25
tgggcccttg gtggaggcag agctcacggt gacc                                  34

<210> SEQ ID NO 26
<211> LENGTH: 33
<212> TYPE: DNA
<213> ORGANISM: Artificial Sequence
<220> FEATURE:
<223> OTHER INFORMATION: forward primer for light chain variable region

<400> SEQUENCE: 26
caggctttca gaggtctaat aggtgatacc aac                                   33

<210> SEQ ID NO 27
<211> LENGTH: 32
<212> TYPE: DNA
<213> ORGANISM: Artificial Sequence
<220> FEATURE:
<223> OTHER INFORMATION: reverse primer for light chain variable region

<400> SEQUENCE: 27
tggtatcacc tattagacct ctgaaagcct gg                                    32

<210> SEQ ID NO 28
<211> LENGTH: 36
<212> TYPE: DNA
<213> ORGANISM: Artificial Sequence
<220> FEATURE:
<223> OTHER INFORMATION: forward primer for light chain variable region

<400> SEQUENCE: 28
gttccgggtg ttcctgccag attctcaggc tccctg                                36

<210> SEQ ID NO 29
<211> LENGTH: 27
<212> TYPE: DNA
<213> ORGANISM: Artificial Sequence
<220> FEATURE:
<223> OTHER INFORMATION: reverse primer for light chain variable region

<400> SEQUENCE: 29
ggagcctgag aatctggcag gaacacc                                          27

<210> SEQ ID NO 30
<211> LENGTH: 28
<212> TYPE: DNA
<213> ORGANISM: Artificial Sequence
<220> FEATURE:
<223> OTHER INFORMATION: forward primer for light chain variable region
```

```
<400> SEQUENCE: 30
tcaggctccc tgattggaga caaggctg                                        28

<210> SEQ ID NO 31
<211> LENGTH: 27
<212> TYPE: DNA
<213> ORGANISM: Artificial Sequence
<220> FEATURE:
<223> OTHER INFORMATION: reverse primer for light chain variable region

<400> SEQUENCE: 31
gagggcagcc ttgtctccaa tcaggga                                         27

<210> SEQ ID NO 32
<211> LENGTH: 342
<212> TYPE: DNA
<213> ORGANISM: Artificial Sequence
<220> FEATURE:
<223> OTHER INFORMATION: variable region of humanized heavy chain HFW141

<400> SEQUENCE: 32
caggtgcagc tgaaacagag cggaccaggc ctagtgaagc cctcacagac cctgtccctc    60
acctgcacag tctctggttt ctcattaagt acctatggtg tacagtgggt tcgccagcct   120
ccaggaaagg gtctggagtg gctgggagtg atatggagtg gtggaaacac agactataat   180
gcagctttca tatccagagt gaccatcagc aaggacacct ccaagaacca gtttcactg    240 aaactgtcca gtgtgactgc tgcagacaca gccgtgtatt attgtgccag agcacggtac   300
ttcgatgtct ggggcgctgg gaccacggtc accgtgagct ct                       342

<210> SEQ ID NO 33
<211> LENGTH: 327
<212> TYPE: DNA
<213> ORGANISM: Artificial Sequence
<220> FEATURE:
<223> OTHER INFORMATION: variable region of humanized light chain
      LFW22-31

<400> SEQUENCE: 33
caggctgttg tgactcagga accttcactc accgtctcac ctggtggtac cgtcacactc    60
acttgtcgct caagtactgg ggctattaca actaataact tgccaactg gttccaacag   120 aaacctggcc aggctttcag aggtctaata ggtgatacca caaccgagt tccgggtgtt   180 cctgccagat tctcaggctc cctgctcgga aacaaggctg ccctcaccat cacaggtgca   240
cagcctgaag atgaggcaga atattattgt gctctatggt acaacaactg ggtgttcggt   300
ggaggaacca aactgactgt cctaggc                                       327

<210> SEQ ID NO 34
<211> LENGTH: 327
<212> TYPE: DNA
<213> ORGANISM: Artificial Sequence
<220> FEATURE:
<223> OTHER INFORMATION: variable region of humanized light chain
      LFW22-312

<400> SEQUENCE: 34
caggctgttg tgactcagga accttcactc accgtctcac ctggtggtac cgtcacactc    60
acttgtcgct caagtactgg ggctattaca actaataact tgccaactg gttccaacag   120 aaacctggcc aggctttcag aggtctaata ggtgatacca caaccgagt tccgggtgtt   180 cctgccagat tctcaggctc cctgattgga gacaaggctg ccctcaccat cacaggtgca   240
```

```
cagcctgaag atgaggcaga atattattgt gctctatggt acaacaactg ggtgttcggt      300
ggaggaacca aactgactgt cctaggc                                         327
```

<210> SEQ ID NO 35
<211> LENGTH: 114
<212> TYPE: PRT
<213> ORGANISM: Artificial Sequence
<220> FEATURE:
<223> OTHER INFORMATION: variable region of humanized heavy chain HFW141

<400> SEQUENCE: 35

```
Gln Val Gln Leu Lys Gln Ser Gly Pro Gly Leu Val Lys Pro Ser Gln
  1               5                  10                  15

Thr Leu Ser Leu Thr Cys Thr Val Ser Gly Phe Ser Leu Ser Thr Tyr
             20                  25                  30

Gly Val Gln Trp Val Arg Gln Pro Pro Gly Lys Gly Leu Glu Trp Leu
         35                  40                  45

Gly Val Ile Trp Ser Gly Gly Asn Thr Asp Tyr Asn Ala Ala Phe Ile
     50                  55                  60

Ser Arg Val Thr Ile Ser Lys Asp Thr Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Arg Ala Arg Tyr Phe Asp Val Trp Gly Ala Gly Thr Thr Val Thr Val
            100                 105                 110

Ser Ser
```

<210> SEQ ID NO 36
<211> LENGTH: 109
<212> TYPE: PRT
<213> ORGANISM: Artificial Sequence
<220> FEATURE:
<223> OTHER INFORMATION: variable region of humanized light chain
      LFW22-31

<400> SEQUENCE: 36

```
Gln Ala Val Val Thr Gln Glu Pro Ser Leu Thr Val Ser Pro Gly Gly
  1               5                  10                  15

Thr Val Thr Leu Thr Cys Arg Ser Ser Thr Gly Ala Ile Thr Thr Asn
             20                  25                  30

Asn Phe Ala Asn Trp Phe Gln Gln Lys Pro Gly Gln Ala Phe Arg Gly
         35                  40                  45

Leu Ile Gly Asp Thr Asn Asn Arg Val Pro Gly Val Pro Ala Arg Phe
     50                  55                  60

Ser Gly Ser Leu Leu Gly Asn Lys Ala Ala Leu Thr Ile Thr Gly Ala
 65                  70                  75                  80

Gln Pro Glu Asp Glu Ala Glu Tyr Tyr Cys Ala Leu Trp Tyr Asn Asn
                 85                  90                  95

Trp Val Phe Gly Gly Gly Thr Lys Leu Thr Val Leu Gly
            100                 105
```

<210> SEQ ID NO 37
<211> LENGTH: 109
<212> TYPE: PRT
<213> ORGANISM: Artificial Sequence
<220> FEATURE:
<223> OTHER INFORMATION: variable region of humanized light chain
      LFW22-312

<400> SEQUENCE: 37

Gln Ala Val Val Thr Gln Glu Pro Ser Leu Thr Val Ser Pro Gly Gly
 1               5                  10                  15

Thr Val Thr Leu Thr Cys Arg Ser Ser Thr Gly Ala Ile Thr Thr Asn
             20                  25                  30

Asn Phe Ala Asn Trp Phe Gln Gln Lys Pro Gly Gln Ala Phe Arg Gly
         35                  40                  45

Leu Ile Gly Asp Thr Asn Asn Arg Val Pro Gly Val Pro Ala Arg Phe
     50                  55                  60

Ser Gly Ser Leu Ile Gly Asp Lys Ala Ala Leu Thr Ile Thr Gly Ala
 65                  70                  75                  80

Gln Pro Glu Asp Glu Ala Glu Tyr Tyr Cys Ala Leu Trp Tyr Asn Asn
                 85                  90                  95

Trp Val Phe Gly Gly Gly Thr Lys Leu Thr Val Leu Gly
            100                 105

<210> SEQ ID NO 38
<211> LENGTH: 5
<212> TYPE: PRT
<213> ORGANISM: Artificial Sequence
<220> FEATURE:
<223> OTHER INFORMATION: heavy chain CDR1

<400> SEQUENCE: 38

Thr Tyr Gly Val Gln
 1               5

<210> SEQ ID NO 39
<211> LENGTH: 16
<212> TYPE: PRT
<213> ORGANISM: Artificial Sequence
<220> FEATURE:
<223> OTHER INFORMATION: heavy chain CDR2

<400> SEQUENCE: 39

Val Ile Trp Ser Gly Gly Asn Thr Asp Tyr Asn Ala Ala Phe Ile Ser
 1               5                  10                  15

<210> SEQ ID NO 40
<211> LENGTH: 6
<212> TYPE: PRT
<213> ORGANISM: Artificial Sequence
<220> FEATURE:
<223> OTHER INFORMATION: heavy chain CDR3

<400> SEQUENCE: 40

Ala Arg Tyr Phe Asp Val
 1               5

<210> SEQ ID NO 41
<211> LENGTH: 14
<212> TYPE: PRT
<213> ORGANISM: Artificial Sequence
<220> FEATURE:
<223> OTHER INFORMATION: light chain CDR1

<400> SEQUENCE: 41

Arg Ser Ser Thr Gly Ala Ile Thr Thr Asn Asn Phe Ala Asn
 1               5                  10

```
<210> SEQ ID NO 42
<211> LENGTH: 7
<212> TYPE: PRT
<213> ORGANISM: Artificial Sequence
<220> FEATURE:
<223> OTHER INFORMATION: light chain CDR2

<400> SEQUENCE: 42

Asp Thr Asn Asn Arg Val Pro
  1               5

<210> SEQ ID NO 43
<211> LENGTH: 8
<212> TYPE: PRT
<213> ORGANISM: Artificial Sequence
<220> FEATURE:
<223> OTHER INFORMATION: light chain CDR3

<400> SEQUENCE: 43

Ala Leu Trp Tyr Asn Asn Trp Val
  1               5
```